United States Patent [19]

Rutherford

[11] Patent Number: 5,069,231

[45] Date of Patent: Dec. 3, 1991

[54] METHOD FOR IMPARTING FUNCTIONAL INGREDIENTS, FUNCTIONAL INGREDIENT-IMPARTING ARTICLES AND METHODS FOR PREPARATION AND USE THEREOF

[75] Inventor: Howard J. Rutherford, Highlands, N.J.

[73] Assignee: International Flavors & Fragrances Inc., New York, N.Y.

[21] Appl. No.: 407,064

[22] Filed: Sep. 14, 1989

Related U.S. Application Data

[63] Continuation-in-part of Ser. No. 379,175, Jul. 12, 1989.

[51] Int. Cl.$^5$ .......................... A24D 3/04; A24D 1/00
[52] U.S. Cl. .................................... 131/335; 131/270; 131/273; 222/187; 106/15.05
[58] Field of Search ............... 131/270, 276, 273, 335; 106/15.05; 222/187

[56] References Cited

U.S. PATENT DOCUMENTS 4,813,437 3/1989 Ray ..................................... 131/270
4,920,989 5/1990 Rose ..................................... 131/220

Primary Examiner—V. Millin
Attorney, Agent, or Firm—Arthur L. Liberman

[57] ABSTRACT

Described are methods for effecting the controlled release of the functional organoleptic materials, to wit:
(a) perfumery materials;
(b) insect attractants;
(c) insect repellents;
(d) animal repellents;
(e) fabric softener compositions;
(f) flavor materials;
(g) surface active agents; and
(h) insect pheromones over a relatively long period of time and, in the same time frame, effecting an initial "Burst" of the same or different organoleptic functional materials over a relatively short period of time. Also described are articles useful in effecting the controlled release of such functional organoleptic materials over a relatively long period of time and in the same time frame effecting an initial "Burst" of the same or different organoleptic functional materials over a relatively short period of time.

39 Claims, 6 Drawing Sheets

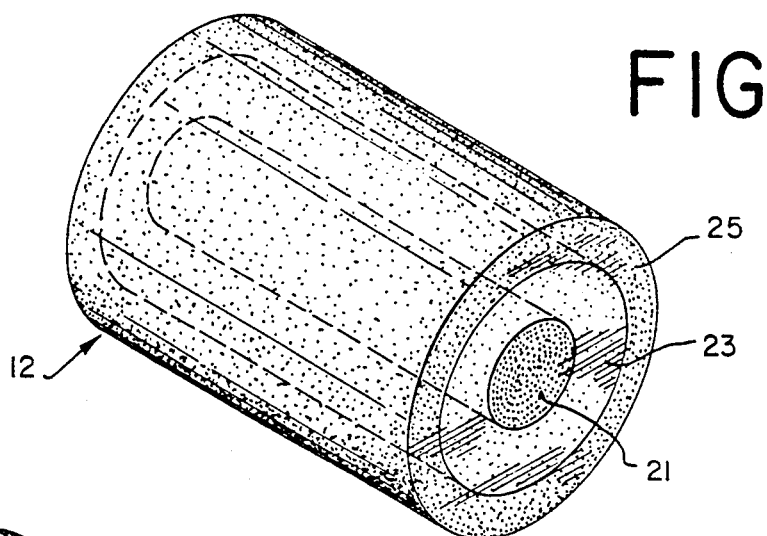
FIG.1-a
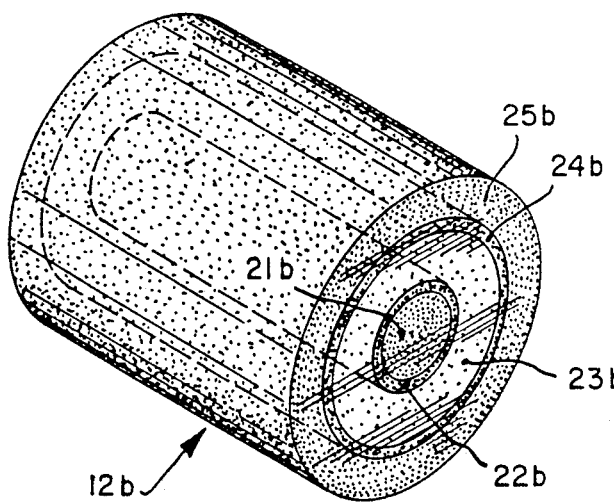
FIG.1-b
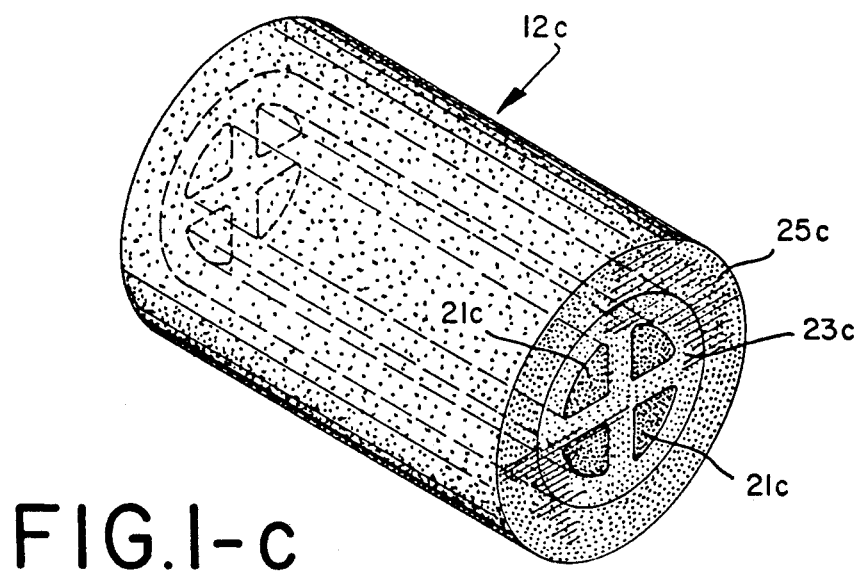
FIG.1-c

FIG. 7
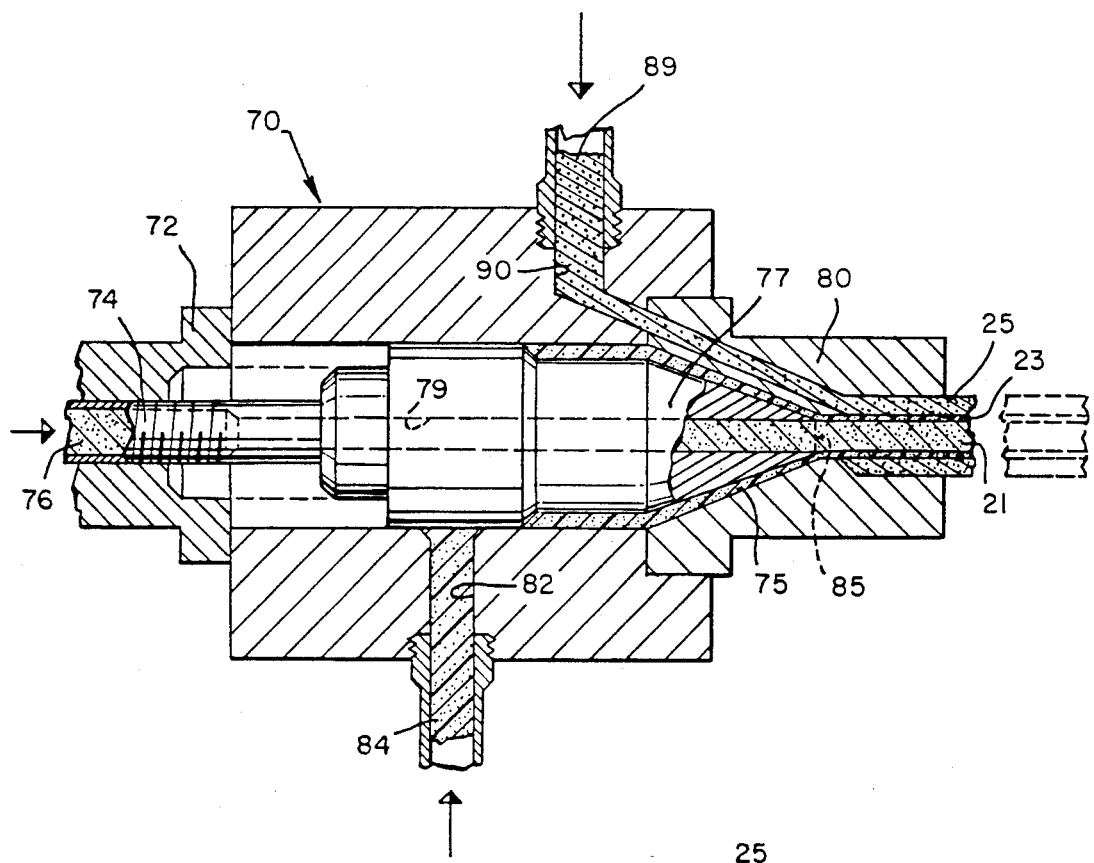
FIG. 7-A
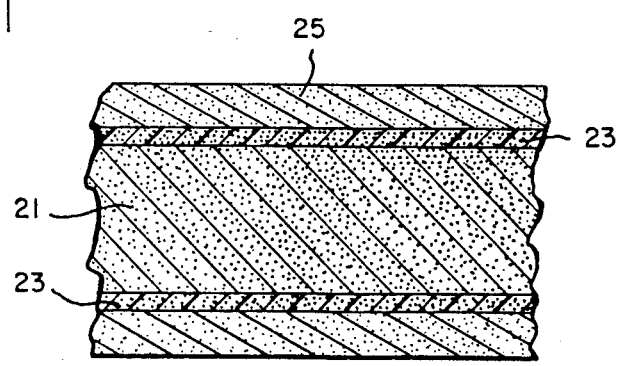

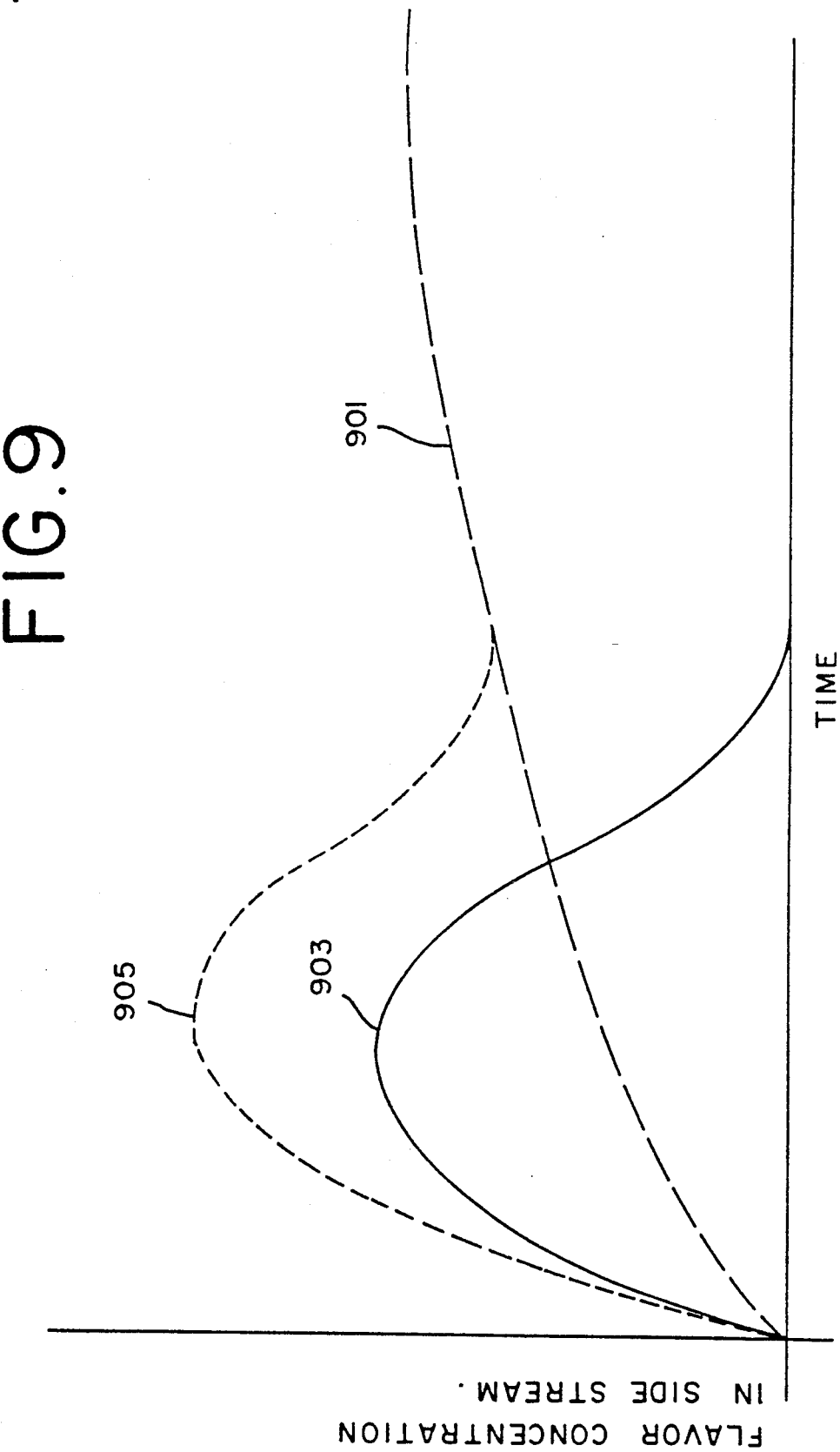

5,069,231

METHOD FOR IMPARTING FUNCTIONAL INGREDIENTS, FUNCTIONAL INGREDIENT-IMPARTING ARTICLES AND METHODS FOR PREPARATION AND USE THEREOF

This application is a continuation-in-part of application for U.S. Pat. Ser. No. 379,175 filed on July 12, 1989.

BACKGROUND OF THE INVENTION

The present invention relates to methods for effecting the controlled release of functional organoleptic materials over a relatively long period of time and in the same time frame effecting an initial "burst" of the same or different organoleptic functional materials over a relatively short period of time. More specifically, it relates to methods for imparting desired flavors and/or aromas in both a controlled manner and in the form of an initial flavor or aroma "burst" or initial high intensity flavor and/or aroma impact to products such as smoking tobacco products, air fresheners and the like through the use of flavor and/or aroma bearing articles, to generally baculiform flavor and/or aroma-bearing articles, and to methods for the preparation and use thereof.

It is frequently desirable to impart flavors and aromas or a combination of flavor and aroma to various consumable and other products. The flavor and aroma compositions and ingredients are by their very nature volatile, and in some case, fleeting. There is thus always the need to provide the aromatic flavoring and aroma compositions in a form which will permit storage prior to use, but which will release the compositions at a desired time, and over a relatively long period of time and in the same time frame, effecting an initial "burst" of the same or different organoleptic functional materials over a relatively short period of time.

As an instance of such a need, the use of flavoring materials in tobacco products such as cigarettes, cigars, pipe tobaccos, and snuff is a practice of long standing in the industry. Flavoring compositions were probably originally added to the tobacco itself. The flavors, for instance, were put into an aqueous solution or combined with glycerol and sprayed on the leaf or onto the chopped leaf, a process also known as top-dressing, and then dried.

There are of course many routes for the addition of flavor materials to tobacco products. They can be added directly to snuff products and to pipe tobaccos when these products are in their final form. In the case of the cigars, the flavors can be added to the wrapper leaf, to the filler, or to both. In the case of cigarettes, the flavor has also been incorporated, in conjunction with the tobacco itself, the cigarette paper, the glue which is used to fasten the paper, and by injecting the flavoring material into the filter pieces or in some instances by putting flavor pellets into the filters during manufacture of the cellulosic filter tow.

One drawback with some of these prior art approaches is that the burning of the glue, paper and the like can create problems with the flavoring material. As the flavor material burns, it may produce unwanted flavors or sidestream aromas and the like. Also, in some instances, the choice of flavoring composition components can be limited by the necessity to avoid the formation of potentially harmful compounds.

Placement of some or all of the flavoring compositions in the filter can obviate some of the problems incurred in putting desired flavor materials in the tobacco, paper, or glue of the cigarette. It has been found, however, that components of the flavoring composition are lost from the filters during storage. Indeed, the largest proportion of the flavor composition can be lost over a period of time. This results in the need to remove the product from consumer channels or to use much larger quantities of flavoring composition or both.

In one approach to the solution of the problem, pellets containing flavoring material have been incorporated into cigarette filters. For example, in menthol cigarettes the menthol has been incorporated into carriers and placed in the filters. The results are adequate, although shelf life is still shorter than is desired. The problem becomes more acute, however, when it is desired to use a flavor like spearmint. In order to get the desired spearmint flavor, materials such as carvone are used, and it is found that the carvone is very volatile, so that it does not remain in the filter for a sufficiently long storage period prior to use.

Other considerations are encountered in the preparation of other articles designed to impart aromas or flavors to goods or to environments. One example of such uses is air fresheners. Many different methods have been developed for the purpose. One of the early forms was a cellulosic or other textile non-woven article which was soaked in or otherwise treated with an aroma composition. It was necessary to tightly package such articles so that the aroma material would not be lost, and of course once the packaging is removed the article will release the aroma composition at an uncontrolled rate until exhausted.

Another type of air freshener involved a wick in a bottle. This enabled the user to control the release of aroma material on an on-off basis by opening the bottle or other container and deploying the wick to permit the aroma material to diffuse into the air. The container is generally heavy and, if of glass, breakable. Also it had to be deployed on a generally flat, horizontal surface, least it fall sideways and permit the aroma material to flow out around the wick, so that there are limitations in placing it in the space where it is to be used.

There are many other schemes and devices for use in air fresheners. The use of a plastic container with a permeable membrane across the top is known. Such a device is limited in the amount of material it can deploy by the surface area of the membrane at the top. Once again, a horizontal surface is required for the device and there is the hazard that the fluid in the interior will simply flow out through the membrane if the container is turned on its side. Scented plastics have been shown, such as those in *Chemical Abstract* 110:116287t.

Yet another instance of the use of such aromatic compositions is in the field of laundering and detergent products where it is desired to have fragrances released during the wash, rinse, and/or drying cycles. The need in this instance is to release one or more aromatic compositions during one or more of the laundering cycles. One method for accomplishing this is set forth in U.S. Pat. No. 4,842,761 which utilizes matrices of different polymers.

THE INVENTION

Accordingly, the present invention provides novel articles for effecting both (i) the controlled release over a relatively long period of time of functional materials like organoleptic compositions, including flavors and/or fragrances into the environment and (ii) in the same time frame an initial "burst" of the same or different functional materials over a relatively short period of time.

Briefly, the methods of the present invention are carried out by use of a novel baculiform or rod-like article which comprises (a) one or more cores containing a first polymeric material in which is dispersed at least one functional organoleptic material with a molecular weight greater than 100 (b) a covering barrier on such core or cores of a second polymeric material having a permeability to the organoleptically functional composition which is substantially less than the permeability of the first polymeric material and (c) a functional material "burst" coating covering the covering barrier, with a selected portion of the core or cores being exposed to the exterior of the article so that the organoleptic composition originally contained within the core or cores is largely retained in the core or cores until it is desired that the functional organoleptic material be controllably released over a relatively long period of time for perception by a user or beneficiary of the product. The novel baculiform articles are also contemplated according to the present invention.

The method of this invention, for instance, permits obtaining (i) a long lasting spearmint-fresh aftertaste when a cigarette is smoked after having been kept on the shelf for a year or longer and (ii) a short term high intensity "burst" of spearmint-fresh aftertaste immediately on the smoking of the cigarette. Similarly, it provides baculiform air freshener articles in which the release of the aroma-imparting composition can be controlled as to rate, intensity and length of use.

In another aspect of the invention, the article can be comprised of (1) a core polymer (2) a first covering polymer and (3) a second covering polymer, which have differing rates of water solubility, so that the first covering, the second covering and the core will dissolve at different rates and provide for release of the functional material, which in this embodiment could also include such materials as fabric softeners, surfactants, anti-static agents, and the like. It will be apparent from the present disclosure that the articles can be used for a wide variety of products. Thus, one or more of such articles can be incorporated into filters such as those for use in cigarettes. The articles of the present invention can also be used in air fresheners and the like. The present invention thus provides methods for modifying the organoleptic properties of a wide variety of products, as will be appreciated by those skilled in the art from the present disclosure.

Thus the present invention simultaneously provides (i)controlled delivery systems and (ii) initial impact high intensity delivery systems in the same article for delivery of organoleptic functional materials or compositions for a variety of uses. In cigarette filter articles, the systems deliver flavor where the "gate" or area through which the controlled release flavor is delivered as disclosed hereinafter is the cut open end of the baculiform article. The "burst" flavor is simultaneously delivered (as shown in FIG. 9). In a controlled delivery-initial impact high intensity delivery system for air fresheners, the gate is again the open cut end. For controlled delivery-initial impact high intensity delivery in a laundry system, a water-soluble material leaches out of the ends while, for example, perfumery material exits from the outer functional material "burst" coating, and further control can also be obtained by the use of various polymers on the exterior. In this case, a barrier coating of polypropylene is more hydrophilic than low-density polyethylene or ethylene-vinyl acetate and a functional ingredient burst coating of ethylene-vinyl acetate is more hydrophilic than high density polyethylene.

The present invention can also be applied to make soluble materials with a water-insoluble barrier film 23, thin with respect to the interior core 21 and the exterior water soluble coating 25. In the case of these water-soluble products, fabric softeners, detergents, bleaches, and other materials such as described in U.S. Pat. No. 4,842,761 could be placed in the interior of the article for release by leaching.

The present invention also contemplates methods for the production of such controlled release/initial burst flavoring and fragrance articles which methods comprise introducing the polymer and the flavoring material, separately or together, into extruder means to form a mixture of the polymer and flavoring composition, drawing the mixture through orifice means to form a generally baculiform extrudate and simultaneously with the drawing of the mixture covering the rodlike extrudate with (1) a barrier material and (2) an initial "burst" material to form two concentric outer coatings substantially coaxial with and on the extrudate to provide the final baculiform article. The extrudate is subsequently cooled in a liquid, and is supplied to the user, e.g., a cigarette or cigarette filter manufacturer in the form of a roll of the baculiform material. Alternatively, as disclosed hereinafter the articles can be furnished in the form of short rods ready for incorporation into or use in a product.

The user can then cut the coil into individual articles for incorporation into the ultimate product which it is desired to flavor. In the case of filter cigarettes, the flavor-modifying rods of this invention can be supplied by cutting the coils into rods with high-speed machinery and continuously supplying the rods to filter materials to incorporate the rods into filter cigarettes. It will be appreciated by those skilled in the art from the present description that the flavor-containing article can also be provided directly in the form of small rods by cutting the extrudate immediately instead of providing it in coil form. The present invention thus also provides methods for altering or enhancing or improving the flavors of consumable materials. In other embodiments of the invention, a baculiform product can be provided in generally larger sizes for incorporation, e.g., into air freshener products. The size of the rod is selected as appropriate for the flavor or fragrance release. In other embodiments, the baculiform articles can be prepared to have the first polymer and second polymer with different solubilities in a selected medium, such as water, so that they can be used in laundering compositions.

The invention is further described by reference to the accompanying drawings, wherein:

FIG. 1a is a view of one embodiment of the baculiform organoleptic article and FIGS. 1b and 1c are views of two other embodiments of the baculiform articles;

FIG. 7 is a schematic view, partially in cross-section, of an extrusion apparatus especially adapted for use in producing the baculiform articles of the invention;

FIG. 7A is a cut-away side elevation view of an enlargement of the extruded material produced using the apparatus of FIG. 7;

Figure 8:
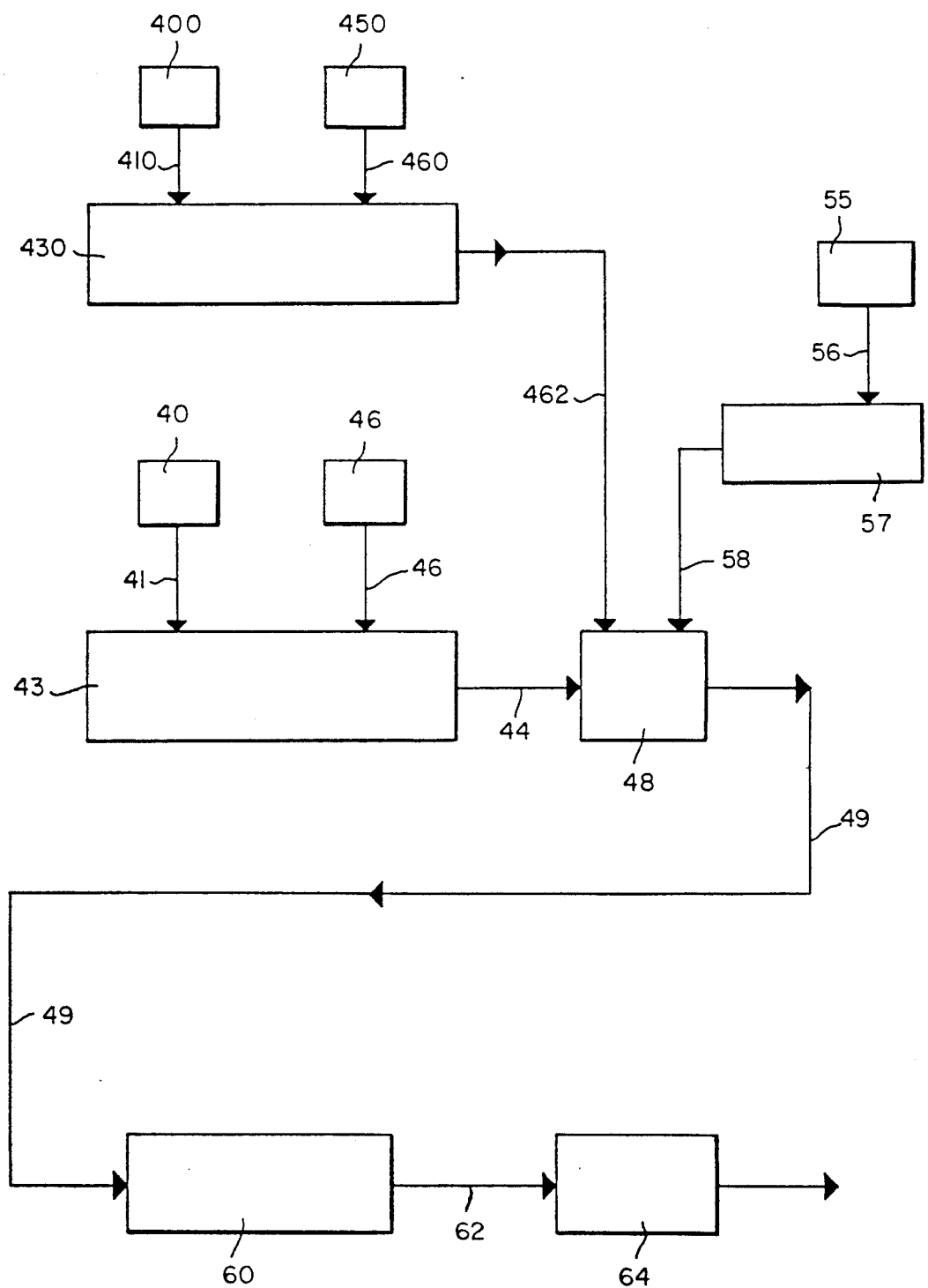

FIG. 8 is a flow diagram of a desired method for the preparation of the baculiform articles according to the present invention; and FIG. 9 is graphical representations of flavor concentration in the side stream (total concentration at graph 905) caused by controlled release (graph 901) and initial flavor "burst" (graph 903) using the articles of FIGS 1a, 1b and 1c.

The polymer core component and the flavor and/or aroma "burst" component of the organoleptic articles of this invention are in general normally solid polymers. The polymer can be the same or different water-soluble polymers in certain aspects of the invention disclosed herein, but it is preferable in certain desired embodiments of the invention that they be water-insoluble. The polymers are chosen so that they are compatible with the organoleptic compositions used and so that they are each materials which do not contain and will not produce during use toxic materials or products. The core polymer as well as the functional ingredient "burst" polymer used to carry the organoleptic functional compositions are relatively more permeable to the constituents of the organoleptic functional composition than the second or barrier polymer and should also be stable to the conditions of use. Thus, if they are to be used in a cigarette filter, they should be capable of withstanding the temperatures, gases and vapors occasioned by the passage of the combustion products through the filter. For air freshener uses the core polymer or polymers and the functional "burst" polymer or polymers should of course be capable of withstanding the conditions of storage and use, that is, among other factors the temperatures and humidities to be encountered.

It will be understood that the filter in which the flavoring rods of this invention are used can be comprised of any materials used in cigarette filters. Filters most usually contain compacted cellulosic material which is produced in several ways. However, such filters can also include other or entirely different components which absorb or adsorb components of the main smoke stream. Sometimes the filters also contain components which will absorb or otherwise capture one or more undesired components of the smoke stream. In any event, the baculiform flavoring articles of the present invention are readily used with all such filter materials.

The normally solid core polymers as well as the functional ingredient "burst" polymers for use herein can include mixtures of various polymers, depending upon the properties desired. Thus, when multiple cores are used in the articles of this invention, the several cores can be comprised of the same or different polymers and these core polymers may be the same as or different from the functional ingredient "burst" polymers. Among the water-insoluble polymers used herein for the core material as well as the functional ingredient "burst" polymers are low-density polyethylene, high-density polyethylene, copolymers of ethylene acetate and vinyl acetate, polypropylene, polyvinyl chloride, cellulose acetate, methyl cellulose, cellulose acetate-butyrate, polyisobutylene, and the like. Mixtures of 50 to 70 parts of low-density polyethylene and 30 to 10 parts of ethylene vinyl acetate have been found to provide good results, and such mixtures are preferred in certain embodiments of the invention.

An additional property required of (a) the polymer core material and (b) the functional ingredient "burst" polymer material in the production of cigarette filters is stiffness, so that the coil of extrudate can readily be cut by the high-speed machinery used in the manufacture of cigarette. If the core material or the functional ingredient "burst" polymer material are each too stiff, they will cause the cutter blades to wear rapidly and necessitate frequent shutdowns of the machinery to permit blade changes. If the core material and/or the functional ingredient "burst" polymer material are too soft, they will not cut cleanly.

As taught above, the organoleptic material-bearing core is surrounded (i) by a layer of second material which substantially bars passage of the organoleptic material from the core which, in turn, is surrounded (ii) by a functional ingredient "burst" polymer layer. In other words, the permeability of the second material with respect to the organoleptic functional composition is substantially less than that of the core material and substantially less than that of the core material and substantially less than that of the functional ingredient "burst" polymer material. Generally, then, these second polymer barrier materials in desired embodiments of the invention are to be selected to be less previous to the organoleptic compositions and to provide the properties required in the product.

In general, the barrier materials are crystalline polymers. Examples of barrier materials which can be used are polyamides, polyesters, polyvinyl derivatives such as poly vinyl chloride, polyolefins containing three or more carbon atoms, such as polypropylene, polybutylene and the like polyepoxides such as crystalline homopolymers of ethylene oxide or polymers of bisphenol-A with epichlorohydrin, and block polymers such as copolymers of propylene and polyethylene of the polyallomer type, and the like. The polyamides are highly crystalline and are preferred in certain embodiments of the invention.

As stated, supra, the functional ingredient "burst" polymer coating on the barrier material includes polymers similar in permeability characteristics to the core polymers. The preferred polymer is polyethylene-vinyl acetate.

It will be understood according to the present invention that there is considerable latitude in formulating baculiform articles according to the present invention. When the articles are to be used for inclusion in cigarette filters, there is a need to maintain a relatively small size and properties which fit the articles for high-speed production. For cigarette filter baculiform flavoring articles, they must adequately deliver the flavor immediately and over the time that the cigarette is being smoked. For air fresheners, only a small quantity of material need be released over a relatively short period of time, but there should be a long-term release of the organoleptic substance. On the other hand, baculiform articles for air freshener uses do not have the same size restrictions in all embodiments, so they can be larger. Moreover, the air freshener is expected to deliver a larger quantity of total fragrance material over a longer period of time. The articles of the present invention used in air fresheners yield an initial burst of air freshener or perfuming material and, in addition, flatten the release rate so that the organoleptic composition is released over a longer term in a "controlled release"

manner. The present invention accordingly provides means for controlling the release of the flavor and/or aroma composition contained in the core and at the same time effects an initial flavor or aroma burst which is desired and/or required by the ultimate consumer for a wide variety of uses.

If desired, the barrier coating may actually comprise two or more individual coatings designed to exploit the properties of two or more different materials. Thus, if a good barrier material is not satisfactorily adhesive to the core material, an additional intermediate adhesive coating can be used to adhere the barrier coating to the core. By the same token if a functional ingredient burst polymer material is not satisfactorily adherent to the barrier layer an additional intermediate adhesive coating can be used to adhere the functional ingredient burst polymer coating to the barrier coating. The coatings can also contain a layer serving to improve the processability of the extrudae of organoleptic composition-bearing extrudate. Such adjuvant materials for the barrier layer include lubricants for the cutter blades of the machinery, or surface rougheners so that the cut rods would not stick or jam in the high-speed cigarette processing equipment, such as that mentioned above. Similarly, such additional coatings, processability improvers, intermediate coatings, rougheners, lubricants, and other processing adjuvants can be used to produce baculiform products for air fresheners, laundry compositions, and the like.

The barrier coating thickness and the functional ingredient burst polymer coating thickness can each be varied around the outside of the rod.

The barrier coating thickness will vary depending upon the organoleptic composition, the particular polymer or other materials (e.g., inorganic mineral materials like calcium carbonate) used in the coating, the ratio of length to diameter of the rods, the particular use to which the articles are to be put, and the like.

The functional ingredient burst polymer coating thickness will vary depending on the length of time that the baculiform article is intended to be stored prior to use and the time period that it is desired to have the initial high-intensity "burst" of functional ingredient last. It will thus be appreciated from the present description that it is possible to vary the thickness or presence of the barrier coating. Thus, if the diametral dimension or along the length, the organoleptic composition release properties can be varied to provide the desired functional activity. Thus, comminuted calcium carbonate or other minerals can be incorporated in the coating. This has the effect of opening an additional "gate" for the system.

One of the important aspects of the present invention as utilized for the preparation of organoleptically functional articles and methods is the ratio of cross-sectional size to length of the article. The rods are generally circular in shape, but need not be so. The actual cross-sectional shape of the rod can be varied so long as the ratio of cross-sectional size to length is maintained. In the case of a circular cross-section, the cross-sectional size or dimension will be the diameter.

The ratio of cross-sectional size of the core to the length of the article can readily be used to control the quantity and rate of release. In effect, there is a "gate" which is controlled by selecting the ratio of surface area of the side of the rod to the surface area of the two ends of the core. The surface area of the ends is important because this is the area through which the vast majority of functional organoleptic composition will be controllably released (over a relatively long period of time) from the core during use. The length of the rod and the cross-sectional dimension will also determine the volume of core and thus to some extent that quantity of functional organoleptic composition which the baculiform article will carry which is intended for controlled release of the functional material over a relatively long period of time.

When the rods of the present invention are used in cigarette filters, it has been found that the ratio of core cross-sectional dimension to overall length is readily adjusted to control the controlled release of the flavor and/or aroma composition from the core. There is a marked variation of release of the flavor or aroma composition from the core when there is no barrier coating on the material. It is generally found that the curve of weight lost per weight of sample is very steep for the core without barrier coating (as it is for the functional ingredient burst polymer layer). By contrast, when the size of the gate is reduced, the curve of weight lost per weight of sample becomes increasingly flat after the functional ingredient from the functional ingredient burst polymer layer is expended.

The size of the article can also be adjusted and controlled to provide the requisite storage retention and the desired controlled release delivery of organoleptic composition (from the core) during smoking in the cigarette. Thus, the overall diameter can be adjusted from as little as 0.05 inches to about 0.3 inches in overall cross-sectional dimension. For an air freshener product the overall size is generally larger than 0.1 inches. In certain desirable air freshener embodidents, the size can range up to one inch. In any case the gate size, that is, 100 times the ratio of the area of the core portion or core portions communicating with the exterior of the article to the overall area of the article, can range from about 4 to about 35. A gate of less than 4 can be used in some embodiments, but ingredient or ingredients of the flavor or fragrance composition is too slow (after the functional ingredient from the functional ingredient burst polymer layer is expended). A gate larger than 35 generally results in the controlled release loss of flavor or aroma composition from the core which is too rapid and which as too steep a curve.

It is accordingly desirable that the gate be from bout 4 to about 30. In certain preferred embodiments of the invention, the gate is from about 5 to about 25.

In certain preferred embodiments, the baculiform article has a substantially cylindrical core coaxial with the coating of second barrier polymer and coaxial with the functional ingredient burst polymer coating. The two oppositely located cross-sectional areas of core are relatively small with respect to the longitudinal area of the core, $2\pi RL$, with the ratio $L/R$ being greater than 10. R is the radius of the core material and is the length of the baculiform article. In another preferred embodiment, the baculiform article comprises a plurality of cores having their axes parallel contained within a substantially cylindrically-shaped barrier polymer, the outer surface of which is longitudinally parallel to the axes of each of the plurality of cores. In another embodiment, there are n cores and each of the cores has exposed at opposite ends cross-sectional areas, A, the totality of areas, nA, of which is area, $2\pi XL$, of the barrier polymer, with the ratio of $XL/R^2n$ being greater than 10. R is the radius of each core and X is the external radius of the barrier polymer cylinder.

FIG. 1a shows one preferred embodiment of a baculiform article 12 according to the present invention. Organoleptic baculiform article 12 is comprised of core 21 containing the organoleptic composition surrounded by barrier layer 23 which, in turn, is surrounded by functional material-containing burst coating 25. FIG. 1b shows another embodiment of a baculiform article 12b in which core 21b containing organoleptic composition is surrounded by intermediate layer 22b (thickness exaggerated for clarity) which serves to adhere barrier layer 23b to the core; and in which barrier layer 23b is surrounded by intermediate layer 24b (thickness exaggerated for clarity) which serves to adhere barrier layer 23b to functional material-containing burst coating 25b. FIG. 1c shows a baculiform article 12c having multiple cores 21c bearing organoleptic composition surrounded by barrier layer 23c, which, in turn, is surrounded by functional material-containing burst coating 25c.

Figure 2:
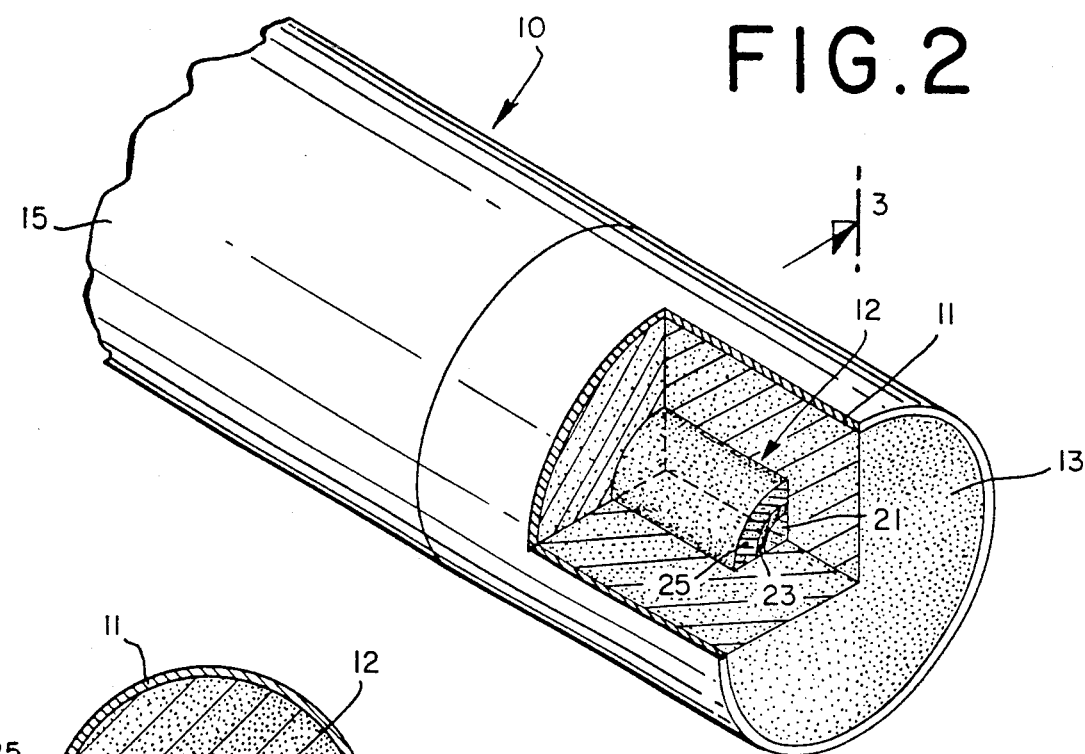
FIG. 2 is a partial sectional view of a cigarette utilizing one embodiment of the baculiform article of the invention.
Figure 3:
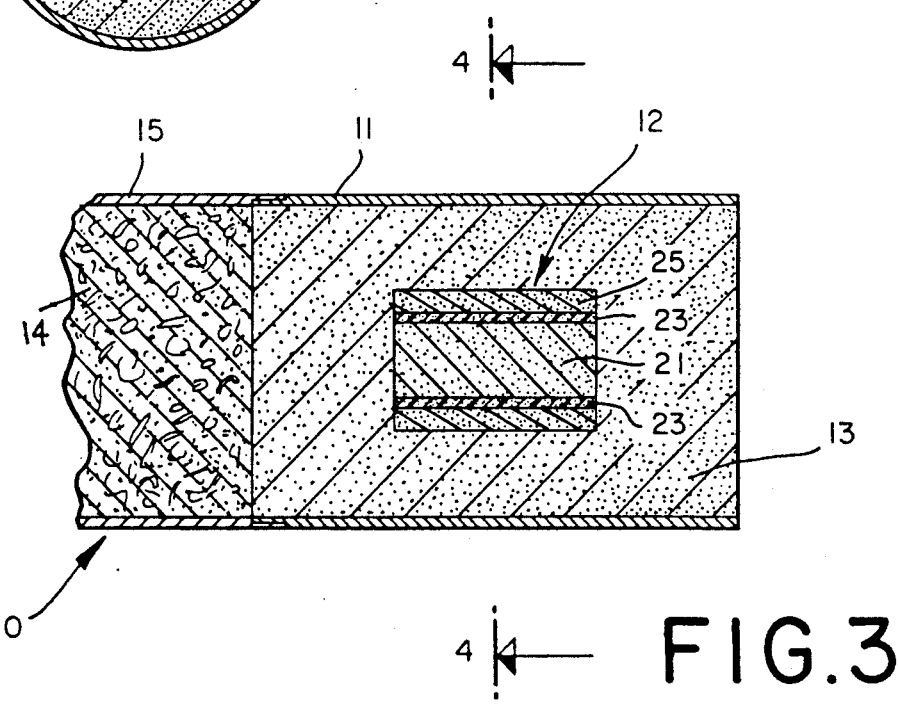
FIG. 3 is a sectional view through 3—3 of FIG. 2.

FIG. 2 shows cigarette 10 comprised of filter 11 and baculiform article 12. FIG. 3 is a sectional view of the same cigarette generally showing filter 11 comprised of cellulosic fibers 13 surrounding article 12. The smoke from tobacco leaf 14 wrapped in paper 15 progresses from the tobacco through the filter. The passage of the smoke from tobacco leaf 14 through filter 11 causes the organoleptic materials in article 12 to be volatilized. In one embodiment of the invention, filter 11 is somewhat more than one inch long and the flavoring rod is about 2.5 millimeters in length by 2.5 millimeters in diameter. In FIGS. 2, 3, 4, 5 and 6 the coating thicknesses are exaggerated for clarity.

Figure 4:
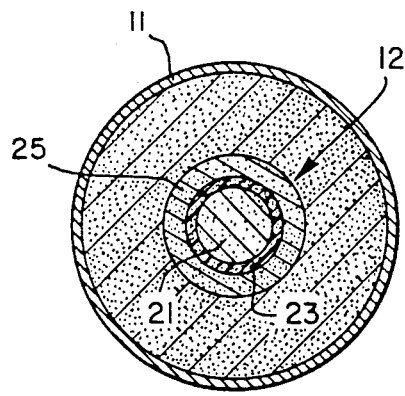
FIG. 4 is a cross-sectional view of the article of FIG. 3 taken at line 4—4.
Figure 5:
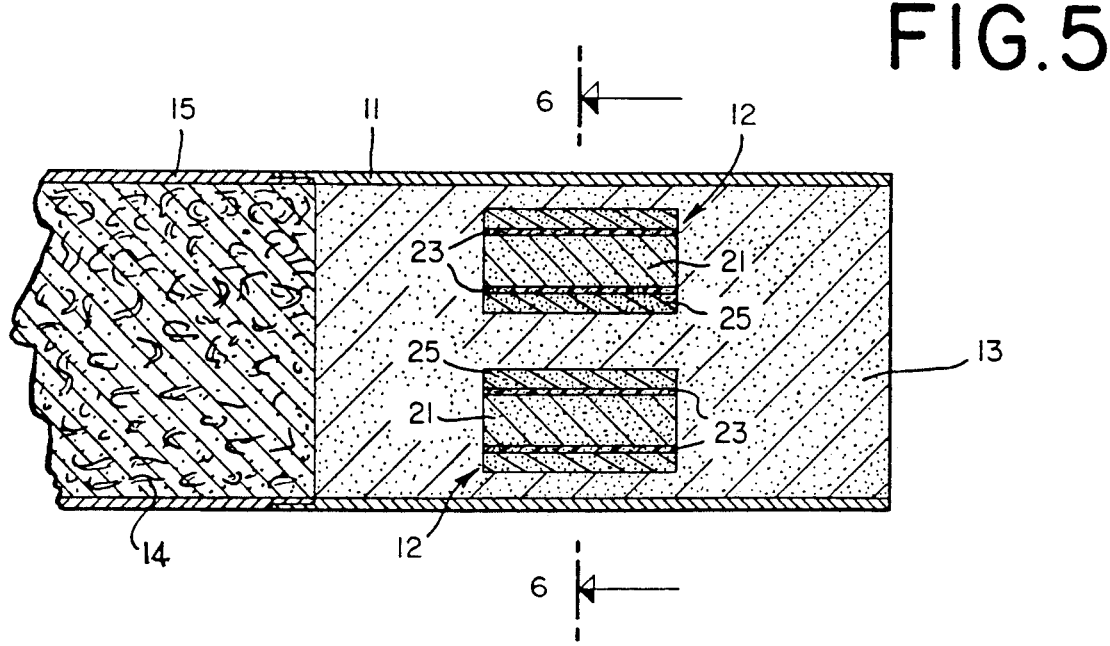
FIG. 5 is a view, partly in cross-section, of a different construction of cigarette filter utilizing a plurality of the articles.
Figure 6:
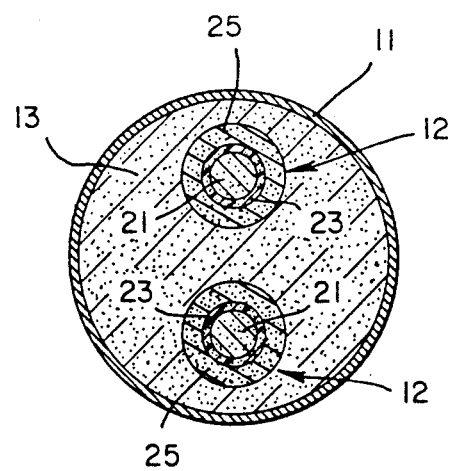
FIG. 6 is a cross-section of FIG. 5 taken at line 6—6.

FIG. 4 shows an embodiment using a plurality of flavoring rods 12 embedded in cellulosic material 13 of filter 11. In some embodiments, this arrangement of flavoring articles provides a more even distribution of flavor across the filter and also releases the flavor from core 21 and from flavor burst coating 25 more rapidly. This is also illustrated in FIG. 5, a section through 5—5 of FIG. 4 showing the baculiform articles 12 in section in cellulosic material 13.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products include those designed or used for smoking such as in cigarette, cigar and pipe tobacco, as well as products such as snuff, chewing tobacco, and the like.

Organoleptic functional compositions as used herein are compositions containing one or more ingredients which affect the flavor and/or aroma of a material as perceived by animals and/or human beings. Such ingredient or ingredients volatilize or otherwise pass into the ambient environment and have an olfactory and/or other sensory effect on the flavor or aroma of the material with which they are associated. Such organoleptic functional compositions broadly include, for example, perfumery materials, insect attractants, animal repellents including insect repellents, flavor materials, and insect pheromones.

Organoleptic functional compositions include saturated, unsaturated, fatty and amino acids; alcohols, including primary and secondary alcohols; esters, carbonyl compounds, including ketones and aldehydes; lactones; cyclic organic materials including benzene derivatives, alicyclics, heterocyclics such as furans, thiazoles, thiazolidines, pyridines, pyrazines and the like; other sulfur-containing materials including thiols, sulfides, disulfides and the like; proteins; lipids; carbohydrates; so-called flavor potentiators; natural flavoring and aroma materials such as cocoa, vanilla, and caramel; essential oils and extracts such as anise oil, clove oil, menthol, carvone and the like; artificial flavoring and fragrance materials such as vanillin; and the like. The active flavoring or aroma ingredient for use in the baculiform articles according to this invention have molecular weights in excess of 100.

Stabilizers for the organoleptic compositions can include preservations such as sodium chloride and the like, antioxidants such as calcium and sodium ascorbate, ascorbic acid, butylated hydroxyanisole, butylated hydroxytoluene, propyl gallate and the like, sequestrants such as citric acid, EDTA, phosphates and the like.

The organoleptic compositions can also include carriers, binders, protective colloids, suspending agents, emulsifiers and the like, such as agar-agar, carrageenan, cellulose and cellulose derivatives such as carboxymethyl cellulose and methyl cellulose and the like, and other proteinaceous materials, lipids, carbohydrates, starches and pectins.

Surface active agents include emulsifying agents such as mono- and/or diglycerides of fatty acids including capric acid, caprylic acid, palmitic acid, myristic acid, oleic acid and the like, lecithin, defoaming and organoleptic composition-dispersing agents such as sorbitan monostearate, potassium stearate hydrogenated tallow alcohol, and the like.

The organoleptic compositions can also include buffers and neutralizing agents such as sodium acetate, ammonium bicarbonate, ammonium phosphate, citric acid, lactic acid, vinegar and the like; colorants such as carminic acid, cochineal, turmeric curcumin, approved food and drug dyes, and the like.

The organoleptic ingredient or ingredients can be combined with one or more vehicles or carriers for adding them to the particular polymer. Vehicles can be edible or otherwise suitable materials such as ethyl alcohol, propylene glycol, water, and the like. Carriers include materials such as gum arabic, carrageenan, other gums, and the like.

The quantity of organoleptic material used will vary depending upon the ultimate product; the amount and type of organoleptic material initially present in the product; the further process or treatment steps to which the product will be subjected; regional and other preference factors; the type of storage, if any, to which the product will be subjected; and the preonsumption treatment. Accordingly, the terminology "effective amount" and "sufficient amount" is understood in the context of the present invention to be quantitatively adequate to alter the organoleptic properties of the tobacco, air freshener, laundering composition, or other material.

All parts, percentages, proportions, and ratios herein are by weight, unless otherwise indicated or clear from the context.

The novel baculiform organoleptic articles of this invention are prepared by extrusion. Referring to FIG. 8, the first barrel of extruder 43 is fed from vessel 40 via line 41 with low-density polyethylene which will act as the core material and the third barrel of extruder 43 is fed via line 46 with a mixture of, for example, carvone and menthol from container 45 to provide, for example, a spearmint flavor. After the ingredients are thoroughly mixed so that the organoleptic composition is dispersed in the low-density polyethylene core material, the mixture is forced into coating nozzle 48 (further described with reference to FIGS. 7 and 7a) which is fed via line 58 from extruder 57 with the polypropylene barrier coating material and which is fed via line 462 from extruder 430 with the flavoring burst coating composition, e.g., containing polyethylene and, for example, carvone and menthol. Extruder 57 is supplied with the polypropylene via line 56 from holding vessel 55. Extruder 430 is fed via line 410 from vessel 400 with low-density polyethylene which will act as the flavor burst coating material and the third barrel of extruder 430 is fed via line 460 from container 450 with a mixture of carvone and menthol to provide for a spearmint flavor. As the mixture of low-density polyethylene and organoleptic composition is drawn through coating nozzle 48, it is uniformly covered with polypropylene having a thickness of 3 mils (0.003 inches), which, in turn, is simultaneously uniformly covered with low-density polyethylene having a thickness of 3 mils (0.003 inches), for example.

Following emergence of the doubly coated material from nozzle 48, it is passed by line 49 to cooling means 60. The cooling means can be a water bath if the components of the product are not water-soluble or it can be a refrigerated chamber or a belt which passes through a cooled refrigerated chamber. After cooling the product, it can be transversely cut into short rods in cutter 64. Alternatively, the cooled product from line 62 can be coiled for storage or shipment. In any event, after the storage or shipment the coils are not cut into individual rods for use as described herein.

One preferred apparatus for preparing the articles according to this invention is shown in FIGS. 7 and 7a. This is a coating nozzle 70 on the end of the barrel of extruder 43 (of FIG. 8) in the embodiment shown. The coaxial final extrusion is adjusted as shown in FIGS. 7 and 7a to control the thickness of (i) the barrier layer coating on the outside of the flavor and/or aroma-containing core and (ii) the functional ingredient burst polymer coating.

Referring to FIG. 7 partially in section above centerline, body 72 is attached to the end of the extruder barrel (not shown), and screw means 74 is used to adjust gap 75 by moving double cone 77 backward and forward along the center line thereof. Organoleptic composition-containing mixture 76 used to form the core is fed through the center of double cone 77 via channel 79 and emerges into drawplate 80 at cone tip 85. Polypropylene barrier material 84 is fed to nozzle 70 through channel 82 from whence it is forced through circumferential gap 75 to coat the organoleptic composition-containing material as the latter emerges from cone tip 85. Low-density polyethylene flavor burst coating material 89 is fed to nozzle 70 through channel 90 from whence it is forced through circumferential gap 75 to coat the barrier material 84 as the latter emerges from cone tip 85. There is thus provided from drawplate 80 a coaxially coated core 21 of organoleptic composition and first polymer, the core being coated with the polypropylene coating barrier layer 23 and the polypropylene barrier layer 23 being coated with flavor burst layer 25.

It will be understood from the present disclosure that multiple baculiform shapes such as rods or even filaments can be extruded to provide the core, with each extrusion coated with (i) the barrier material and (ii) the flavor burst material to obviate loss of the organoleptic composition from the core material.

In certain embodiments, it can be useful to extrude the material with nitrogen taken alone or in combination with, for example, steam to create a cellular structure in the core. This would facilitate vaporization of the organoleptic composition during use. It is desirable in certain embodiments that the baculiform aroma or flavoring article have a substantially round cross-section, although in other embodiments the cross-section can be elliptical or even dumb-bell-shaped with two thicker regions being joined by a thinner connecting region or cruciform with four thicker areas being connected by thinner webs of the core material.

The following example is given to illustrate an embodiment of the invention as it is presently preferred to practice it. It will be understood that this example is illustrative, and the invention is not to be considered as restricted thereto except as indicated in the appended claims.

EXAMPLE I

With the apparatus set forth in FIG. 7 a rod is extruded utilizing as a core (21) 50 parts of low-density polyethylene, 30 parts of ethylene vinyl acetate, and 20 parts of flavoring composition. The rod is extruded in substantially round cross-section and is simultaneously coated with a 5-mil barrier layer of polypropylene, which, in turn, is coated with a 5-mil burst layer 25 of a mixture of 50 parts ethylene vinyl acetate and 50 parts of the same flavoring composition as included in the core. The extrudate is introduced into a water bath to cool the extrudate to a temperature of 25° C.

The flavoring composition used in this example is 15 parts of menthol and 5 parts of isopropyl myristate. The isopropyl myristate functions to keep the organoleptic composition in the core and in the burst layer in an even mixture.

The noodle of extrudate obtained is wound onto a reel after cooling.

Cigarette filters are prepared by combining the extrudate with cellulose tow and chopping the 2.5 mm-diameter coiled noodle into 2.5 mm-long rods. The baculiform flavoring articles and tow are then compacted into a cylinder and wrapped in paper to form individual filters which are cut to a length of 20 mm. The flavoring rod-containing filters are then combined with tobacco and wrapped with paper to form a finished cigarette. When the cigarettes are smoked, the smoke has (i) an initial, high-intensity fresh menthol flavor and (ii) a lower intensity long-lasting menthol flavor (as graphically set forth in FIG. 9). Samples of the cigarettes are stored in packages at an atmosphere of 100° F. and 80% relative humidity. This is a very severe test of the ability of the filters to retain flavor. The cigarettes prepared with the organoleptic articles of the present invention are compared after six months with filter cigarettes which originally contained the same amount of menthol and isopropyl myristate. The conventional filter cigarettes had no menthol flavoring after six months in storage, but the cigarettes prepared with the flavoring articles according to the present invention still had a pleasant menthol flavor when smoked, although the flavor (both the initial "burst" flavor and the long-lasting flavor) was judged to e weaker than that in freshly prepared cigarettes containing the baculiform organoleptic articles.

A series of baculiform cigarette filter adjuncts is prepared according to Example I with various dimentions as set forth in Table I. All linear dimensions are inches and all quantities are in milligrams. "Gate" refers to 100 times the ratio of the two open ends of the core to the total area of the article.

TABLE I

|  | EXAMPLE | | | | | |
| --- | --- | --- | --- | --- | --- | --- |
|  | I-2 | I-3 | I-4 | I-5 | I-6 | I-7 |
| Outside Diameter | .110 | .110 | .090 | .090 | .072 | .072 |
| Barrier Coating | .005 | .005 | .005 | .005 | .005 | .005 |
| Burst Coating Thickness | .005 | .005 | .005 | .005 | .005 | .005 |
| Interior Diameter | .090 | .090 | .070 | .070 | .052 | .052 |
| Length | .100 | .122 | .157 | .203 | .263 | .366 |
| Gate | 27.0 | 24.0 | 16.0 | 13.0 | 7.0 | 5. |
| Weight of Core | 9.9 | 12.1 | 9.4 | 12.2 | 8.6 | 12.1 |
| Total Weight | 14.4 | 17.6 | 14.9 | 19.3 | 15.7 | 21.8 |
| Barrier Coating Weight | 2.2 | 2.7 | 2.7 | 3.5 | 3.5 | 4.7 |
| Burst Coating Weight | 2.3 | 2.8 | 2.8 | 3.6 | 3.6 | 4.9 |

It will be understood from the present description that the barrier coating can be a soluble material, so that when the article is immersed in a fluid such as the water being used for laundry purposes, the coating will dissolve in the rinse cycle and thereby release an aroma composition from the baculiform article.

Thus, the functional organoleptic materials can be perfume compositions, insect attractant compositions, insect repellent compositions, animal repellent compositions, fabric softener compositions, flavor compositions, surface active agents, insect phermones, and the like. The surface active agents suitable for use in the baculiform articles include solid or liquid materials. They can be anionic, cationic, nonionic, and/or zwitterionic.

What is claimed is:

1. An article capable of effecting controlled release of a functional material therefrom into the environment surrounding the article consisting of:
   (a) a core or a plurality of cores consisting of the same or different releasable functional materials dispersed within a first polymeric substance;
   (b) coated onto a substantial portion of the surface of the core or cores, a barrier polymer coating consisting of a second polymeric substance, the second polymeric substance having a permeability to the mass transport of functional material contained within the core or within one or more of the plurality of cores which is substantially less than the permeability of the first polymeric substance to the mass transport; and
   (c) coated onto a substantial portion of the outer surface of the barrier polymer coating, a functional material-burst coating consisting of one or more of the same or different functional material dispersed within a third polymeric substance;
   (i) a portion of the total surface area of the core or cores being directly in contact with the environment surrounding the article;
   (ii) the average molecular weight of each of the functional being greater than about 100;
   (iii) the totality of the outer surface of the functional material-burt coating being directly in contact with the environment surrounding the article; and
   (iv) the functional materials in the core being the same as or different from the functional materials in the functional material-burst coating.

2. The article of claim 1 containing one core and wherein the core, the barrier polymer coating and the functional material-burst coating are coaxial.

3. The article of claim 2 wherein the core and the functional material-burst coating each contains a tobacco flavorant.

4. The article of claim 2 wherein the core consists of a water soluble polymer admixed with a surfactant or fabric softener and the functional material-burst coating contains a perfumery material.

5. The article of claim 2 wherein the core consists of a water soluble polymer admixed with a solid or liquid anionic, cationic, nonionic or zwitterionic surfactant and the functional material-burst coating contains a perfumery material.

6. The article of claim 2 wherein the core has two oppositely located cross-section areas, the totality of which is relatively small with respect to the longitudinal area of the core, $2\pi RL$, with the ratio $L/R$ being greater than ten; wherein L is the lateral length of the article and R is the radius of the core.

7. The article of claim 6 wherein the barrier polymer is solely coated onto the longitudinal area of the core and the entirety of the cross-sectional area, A, is uncoated and exposed to the environment surrounding the article, the two oppositely-located areas, A, being the gate areas, and the ratio of gate areas to longitudinal area being the gate ratio.

8. The article of claim 7 wherein the gate ratio is from about 4 to about 35.

9. The article of claim 7 wherein the gate ratio is from about 5 to about 25.

10. The article of claim 6 wherein both the core and the functional material-burst coating each contains the same or different chemically compatible functional materials selected from the group consisting of:
    (a) perfumery materials;
    (b) insect attractans;
    (c) insect repellents;
    (d) animal repellents;
    (e) fabric softener compositions;
    (f) flavor materials;
    (g) surface active agents; and
    (h) insect pheromones.

11. The article of claim 10 wherein the core contains the same or different polymer selected from the group consisting of:
    (a) low density polyethylene;
    (b) high density polyethylene;
    (c) a copolymer of ethylene and vinyl acetate;
    (d) polypropylene;
    (e) polyvinyl chloride;
    (f) cellulose acetate;
    (g) methyl cellulose;
    (h) cellulose acetate-isobutyrate;
    (i) polyethylene oxide;
    (j) polyisobutylene; and
    (k) polystyrene.

12. The article of claim 6 wherein the core and the functional material-burst coating each contains a tobacco flavorant.

13. The article of claim 6 wherein the core and the functional material-burst coating each consists of a water soluble polymer admixed with a surfactant or a fabric softener.

14. The article of claim 6 wherein the core and the functional material-burst coating each consists of a water soluble polymer admixed with a solid or liquid anionic, cationic, nonionic or zwitterionic detergent.

15. The article of claim 2 wherein the core is a solid cylinder, the barrier polymer coating is cylindrical and the functional material-burst coating is cylindrical.

16. The article of claim 1 wherein the functional material contained within the core or cores is a perfumery material and the functional material contained within the functional material-burst coating is a perfumery material.

17. The article of claim 1 wherein the functional material contained within the core or cores is an insect repellent and the functional material contained within the functional material-burst coating is an insect repellent.

18. The article of claim 1 wherein at least one core and the functional material-burst coating each contains each at least one chemically compatible functional material selected from the group consisting of:
(a) perfumery materials;
(b) insect attractants;
(c) insect repellents;
(d) animal repellents;
(e) fabric softener compositions;
(f) flavor materials;
(g) surface active agents; and
(h) insect pheromones.

19. The article of claim 1 wherein the core or cores contains the same or different polymer selected from the group consisting of:
(a) low density polyethylene;
(b) high density polyethylene;
(c) a copolymer of ethylene and vinyl acetate;
(d) polypropylene;
(e) polyvinyl chloride;
(f) cellulose acetate;
(g) methyl cellulose;
(h) cellulose acetate-isobutyrate;
(i) polyethylene oxide;
(j) polyisobutylene; and
(k) polystyrene.

20. The article of claim 19 wherein the functional material-burst coating contains the same or different polymer selected from the group consisting of:
(a) low density polyethylene;
(b) high density polyethylene;
(c) a copolymer of ethylene and vinyl acetate;
(d) polypropylene;
(e) polyvinyl chloride;
(f) cellulose acetate;
(g) methyl cellulose;
(h) cellulose acetate-isobutyrate;
(i) polyethylene oxide;
(j) polyisobutylene; and
(k) polystyrene.

21. The article of claim 1 wherein a plurality of cores are commonly contained, parallel to one another, within a substantially cylindrically-shaped barrier polymer, the outer surface of which barrier polymer is longitudinally parallel to the axes of each of the plurality of the cores.

22. The article of claim 21 having n cores wherein each of the cores has two oppositely located cross-sectional areas, A, the totality, nA, of which is relatively small with respect to the longitudinal outer surface area of the barrier polymer, $2\pi XL$, with the ratio $(XL/R^2n)$ being greater than ten; wherein L is the lateral length of the article; R is the radius of each of the cores and X is the external radius of the barrier polymer cylinder.

23. The article of claim 22 wherein the barrier polymer is solely coated onto the entireties of each of the longitudinal surfaces of each of the cores and the entirety of the cross-sectional areas, nA, is uncoated and exposed to the environment surrounding the article, the two oppositely-located areas, A, being gate areas, and the ratio of gate areas to longitudinal area being the gate ratio.

24. The article of claim 23 wherein the gate ratio is from about 4 to about 35.

25. The article of claim 23 wherein the gate ratio is from about 5 to about 25.

26. In a cigarette comprising tobacco, cigarette paper, and a filter, the improvement comprising incorporating into the filter one or more articles defined according to claim 1, each of which is a baculiform flavoring adjunct with controlled flavor release to modify the taste of the cigarettes, each adjunct comprising (i) a polymeric core containing a first aromatic flavoring composition with at least one active first flavoring ingredient having a molecular weight greater than 100; (ii) a barrier material coating thereon which substantially bars passage of the flavoring composition therethrough; and (iii) a flavoring-burst coating thereon containing a second aromatic flavoring composition with at least one active second flavoring ingredient, the same as or different from said first flavoring ingredient having a molecular weight greater than 100; the core having a relatively small cross-section and a relatively great length, the gate ratio of cross-section dimention of the core to the length being such that the first flavoring composition is controllably released over a relatively long period of time upon the smoking of the cigarette and the loss of flavoring composition is substantially flat prior to use; and the second flavoring composition being initially released over a relatively short period of time upon the smoking of the cigarette.

27. A cigarette according to claim 26 wherein the gate ratio is from 4 to 35.

28. A cigarette according to claim 26 wherein the gate ratio is from 5 to 25.

29. A cigarette according to claim 26 wherein the core and the flavoring-burst coating are each comprised of low-density polyethylene and ethylene vinyl acetate.

30. A cigarette according to claim 26 wherein the barrier material coating is a substantially crystalline polymer.

31. A cigarette according to claim 26 wherein the barrier material coating is a polyamide, a polyester, a polyvinyl derivative, or a polyolefin prepared from olefin containing three or more carbon atoms and a block copolymer of the polyallomer type.

32. A cigarette according to claim 26 wherein the first flavoring composition comprises menthol, carvone, or mixtures thereof and a vehicle and the second flavoring composition is the same as or different from the first flavoring composition and comprises menthol, carvone, or mixtures thereof and a vehicle.

33. The article of claim 1 which is a baculiform article with controlled flavor and/or aroma release and with initial flavor and/or aroma burst release which comprises (i) a polymeric core containing a first organoleptic functional organoleptic composition with at least one first active organoleptic ingredient having a molecular weight greater than 100; (ii) a barrier material coating thereon which substantially bars passage of the organoleptic functional composition therethrough; and
(iii) a flavoring and/or aroma burst coating composition coated thereon with at least one second active organoleptic functional composition with at least one second active organoleptic having a molecular weight greater than 100, the core having a relatively small cross-section and a relatively great length, the gate ratio of cross-section dimention of the core to the length being such that the first organoleptic composition is controllably released over a relatively long period of time upon use of the article and the loss of flavoring and/or aroma composition from said core is substantially flat prior to use and the second organoleptic composition is initially released over a relatively short period of time on use.

34. A method for modifying the flavor of filter cigarettes which comprises including in the filter at least one baculiform article according to claim 33.

35. A method according to claim 34 wherein one or two baculiform articles are incorporated into the filter.

36. A method according to claim 34 wherein a single baculiform article is incorporated into the filter.

37. The article of claim 1 wherein the second polymeric substance is selected from the group consisting of:
  (a) polyamides;
  (b) polyvinylidene dichloride;
  (c) polyvinyl alcohol;
  (d) high density polyethylene;
  (e) polypropylene; and
  (f) crystalline epoxy resins.

38. The process of claim 37 wherein adhesive layers are caused to be coaxially coextruded between the innermost coextruded sustance and the second polymeric substance; and between the second polymeric substance and the outermost coextruded substance.

39. A process for forming the article of claim 1 comprising the steps of:
  (i) admixing a first functional organoleptic material with a first polymeric substance having a relatively high permeability to the mass transport of the functional material;
  (ii) coaxially coextruding (a) a second polymeric substance having a permeability to the mass transport of the functional material which permability is substantially lower than the permeability of the first polymeric substance; and (b) a second functional organoleptic material with a third polymeric substance having a relatively high permeability to the mass transport of the functional material; with the first polymeric substance whereby the outer most coextruded substance is the third polymeric substance and the innermost coextruded substance is the first polymeric substance, thereby forming a coaxial product;
  (iii) cooling the coaxial product; and
  (iv) substantially transversely severing the coaxial product.

* * * * *